United States Patent
Ryu et al.

(10) Patent No.: US 9,781,938 B2
(45) Date of Patent: Oct. 10, 2017

(54) METHOD FOR ELICITING PLANT IMMUNE RESPONSES BY SEED PRIMING OF HEAT-TREATED BACILLUS CULTURE SOLUTION

(71) Applicant: KOREA RESEARCH INSTITUTE OF BIOSCIENCE AND BIOTECHNOLOGY, Daejeon (KR)

(72) Inventors: Choong Min Ryu, Daejeon (KR); Geun Cheol Song, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 14/443,059

(22) PCT Filed: Nov. 13, 2013

(86) PCT No.: PCT/KR2013/010295
§ 371 (c)(1),
(2) Date: May 14, 2015

(87) PCT Pub. No.: WO2014/077581
PCT Pub. Date: May 22, 2014

(65) Prior Publication Data
US 2015/0289515 A1 Oct. 15, 2015

(30) Foreign Application Priority Data

Nov. 14, 2012 (KR) .................. 10-2012-0128531

(51) Int. Cl.
*A01N 63/00* (2006.01)
*C12N 1/20* (2006.01)
*C12R 1/07* (2006.01)

(52) U.S. Cl.
CPC ............... *A01N 63/00* (2013.01); *C12N 1/20* (2013.01); *C12R 1/07* (2013.01)

(58) Field of Classification Search
None
See application file for complete search history.

(56) References Cited

U.S. PATENT DOCUMENTS

2003/0082792 A1* 5/2003 Bergstrom ............. A01N 63/00
435/252.5

FOREIGN PATENT DOCUMENTS

| KR | 10-0678615 B1 | 1/2007 |
| KR | 10-0860726 B1 | 9/2008 |
| KR | 2012-0075936 A | 7/2012 |
| WO | 2010-109436 A1 | 9/2010 |

OTHER PUBLICATIONS

Buensanteai et al. Thai J. Agricultural Sciences vol. 41, pp. 101-116; publication year: 2008.*
Boylan et al. Mol Gen Genet vol. 212; pp. 271-280; publication year: 1988.*
Wimalaratne et al. Food and Bioproducts Processing vol. 86 pp. 312-316; publication year: 2008.*
International Search Report for PCT/KR2013/010295.
Buensanteai, Natthiya et al., Priming, signaling, and protein production associated with induced resistance by Bacillus amyloliquefaciens KPS46, World Journal of Microbiology and Biotechnology, Jul. 2009, vol. 25, No. 7, pp. 1575-1286. See abstract; pp. 1276, 1277, 1279 and 1282; table 2.
Kloepper, Joseph W. et al., "Induced systemic resistance and promotion of plant growth by *Bacillus* spp", Phytopathology, Nov. 2004, vol. 94, No. 11, pp. 1259-1266. See abstract; pp. 1262 and 1265.

* cited by examiner

*Primary Examiner* — Johann R Richter
*Assistant Examiner* — Katherine Peebles
(74) *Attorney, Agent, or Firm* — The PL Law Group, PLLC

(57) ABSTRACT

The present invention relates to a method of eliciting plant immune responses based on seed priming by using the heat (high temperature)-treated culture solution of *Bacillus* spp, and the high pressure-sterilized culture solution of *Bacillus* sp. strains PB69 and 1628 which have been selected in the present invention exhibits an activity of eliciting induced systemic resistance similar to BTH, and also has an effect for inducing promoted plant growth and controlling plant diseases, and thus it is expected to contribute to enhance the crop productivity.

7 Claims, 6 Drawing Sheets

METHOD FOR ELICITING PLANT IMMUNE RESPONSES BY SEED PRIMING OF HEAT-TREATED BACILLUS CULTURE SOLUTION

CROSS REFERENCE TO RELATED APPLICATIONS

This application is a National Phase application under 35 U.S.C. §371 of International Application No. PCT/KR2013/010295, filed Nov. 13, 2013, which claims priority to and the benefit of Republic of Korea Patent Application No. 10-2012-0128531 filed Nov. 14, 2012, the disclosures of which are incorporated herein by reference in its entirety.

BACKGROUND

Technical Field

The present invention relates to a method for eliciting a plant immune response by seed priming of a *Bacillus* spp. culture solution treated at high temperature. More specifically, it relates to *Bacillus* spp. strains PB69 and 1628 for eliciting induced systemic resistance and promoted plant growth in a plant, a method of eliciting induced systemic resistance and promoted growth in a plant by using high pressure-sterilized culture solution of the aforementioned strains, a method of controlling a plant disease by using high pressure-sterilized culture solution of the aforementioned strains, a composition for eliciting induced systemic resistance and promoted growth in a plant containing, as an active ingredient, high pressure-sterilized culture solution of the aforementioned strains, a composition for controlling plants diseases containing, as an active ingredient, high pressure-sterilized culture solution of the aforementioned strains, a method for treating a seed to elicit induced systemic resistance and promoted growth in a plant by using the aforementioned composition, a method for treating a seed to control plant diseases by using the aforementioned composition, and a primed seed produced by the aforementioned method.

Background Art

Traditionally, methods for inhibiting and controlling an occurrence of plant pathogens have been studied for young plants, and chemically synthesized agrochemicals are mainly used for the methods. However, due to a negative effect of those chemically synthesized agrochemicals on an environment and a human body, their use is now being limited. Further, as an attention is currently paid to the control from a seed stage, studies on development of healthy and strong seeds are actively carried out.

Once rooted, a plant can never move. Thus, in order to have effective response to a change in external environment, a signal transduction system with inside of a plant has been developed. In particular, there is an immune system for fighting against attacks by various pathogens. Such resistant reaction includes induced systemic resistance (ISR) in which resistance is shown not only in a leaf attacked by a pathogen but also in an entire plant which has not been attacked and systemic acquired resistance (SAR) in which resistance is shown for other various pathogens which follow later. Among various agents for inducing SAR, BTH (benzo(1,2,3)-thiadiazole-7-carbothioic acid S-methyl ester, benzothiadiazole) is known as a substance which exhibits the most potent efficacy. However, a serious problem was found for those SAR-inducing agents which have been believed to be useful for overcoming the problems of agrochemicals, i.e., plant growth is inhibited when crops grown in an actual field are treated with them or a harvest amount is significantly lowered compared to a control group with no treatment. From the viewpoint of physiology, this phenomenon was regarded as “allocation fitness cost” phenomenon in which, by expressing many pathogen-related genes even in the absence of pathogens, under limited resources condition plant energy is over-consumed so that plant growth is inhibited as the energy to be used for growth is consumed for having resistance against diseases.

As such, inventors of the present invention selected a *Bacillus* sp. strain which exhibits an activity of eliciting induced systemic resistance similar to BTH and has an effect of promoting plant growth and controlling plant diseases, and tried to determine the seed priming effect of the high pressure-sterilized culture solution of the *Bacillus* sp. strain.

Meanwhile, “*Bacillus* sp. PB25 strain derived from soil and use thereof” is described in Korean Patent Application Publication No. 2012-0075936, and “Microbial polyglucosamine PGB-2 produced and secreted by *Citrobacter* sp. BL4 and use thereof” is disclosed in Korean Patent Registration No. 0678615. However, a method for eliciting a plant immune response by seed priming of heat (high temperature)-treated *Bacillus* culture solution of the present invention has never been disclosed.

SUMMARY

The present invention is devised in view of the circumstances described above. Specifically, the present invention is completed according to the followings: *Bacillus* spp. strains PB69 and 1628, which exhibit an effect similar to BTH (benzothiadiazole) that is known to elicit induced systemic resistance in a plant, were selected, culture solution of each strain was subjected to high pressure-sterilization followed by treatment on seeds of cucumber or pepper, and elicitation of induced systemic resistance and promoted growth in a plant, which is grown from germinated seeds primed before with the high pressure-sterilized culture solution of PB69 or 1628, was confirmed.

In order to solve the aforementioned problems, the present invention provides *Bacillus* sp. strain PB69 for eliciting induced systemic resistance and promoted growth in a plant.

The present invention further provides *Bacillus* sp. strain 1628 for eliciting induced systemic resistance and promoted growth in a plant.

The present invention further provides a method of eliciting induced systemic resistance and promoted growth in a plant comprising:

performing high pressure sterilization of culture solution of the aforementioned *Bacillus* spp. strains PB69 or 1628; and soaking a plant seed in the culture solution of the *Bacillus* spp. strains PB69 or 1628 obtained by high pressure sterilization.

The present invention further provides a method of controlling a plant disease comprising:

performing high pressure sterilization of culture solution of the aforementioned *Bacillus* spp. strain PB69 or 1628; and soaking a plant seed in the culture solution of the *Bacillus* spp. strains PB69 or 1628 obtained by high pressure sterilization.

The present invention further provides a composition for eliciting induced systemic resistance and promoted growth in a plant or controlling a plant disease containing, as an active ingredient, high pressure-sterilized culture solution of the *Bacillus* spp. strain PB69 or 1628.

The present invention further provides a method for treating a seed to elicit induced systemic resistance and promoted growth in a plant or to control a plant disease, comprising soaking a seed in the aforementioned composition for 6 to 18 hours followed by drying.

The present invention still further provides a primed seed produced by the aforementioned method.

According to the present invention, the high pressure-sterilized culture solution of *Bacillus* spp. strains PB69 and 1628 for eliciting induced systemic resistance in a plant has no harmful effect for a human body compared to a chemical agent for treating seeds. Furthermore, as it is obtained by high pressure sterilization, it can continuously induce resistance to various pathogens without having biological deterioration. Furthermore, as it can induce promoted plant growth, it is expected to contribute to increase the crop productivity.

DETAILED DESCRIPTION

Figure 1:
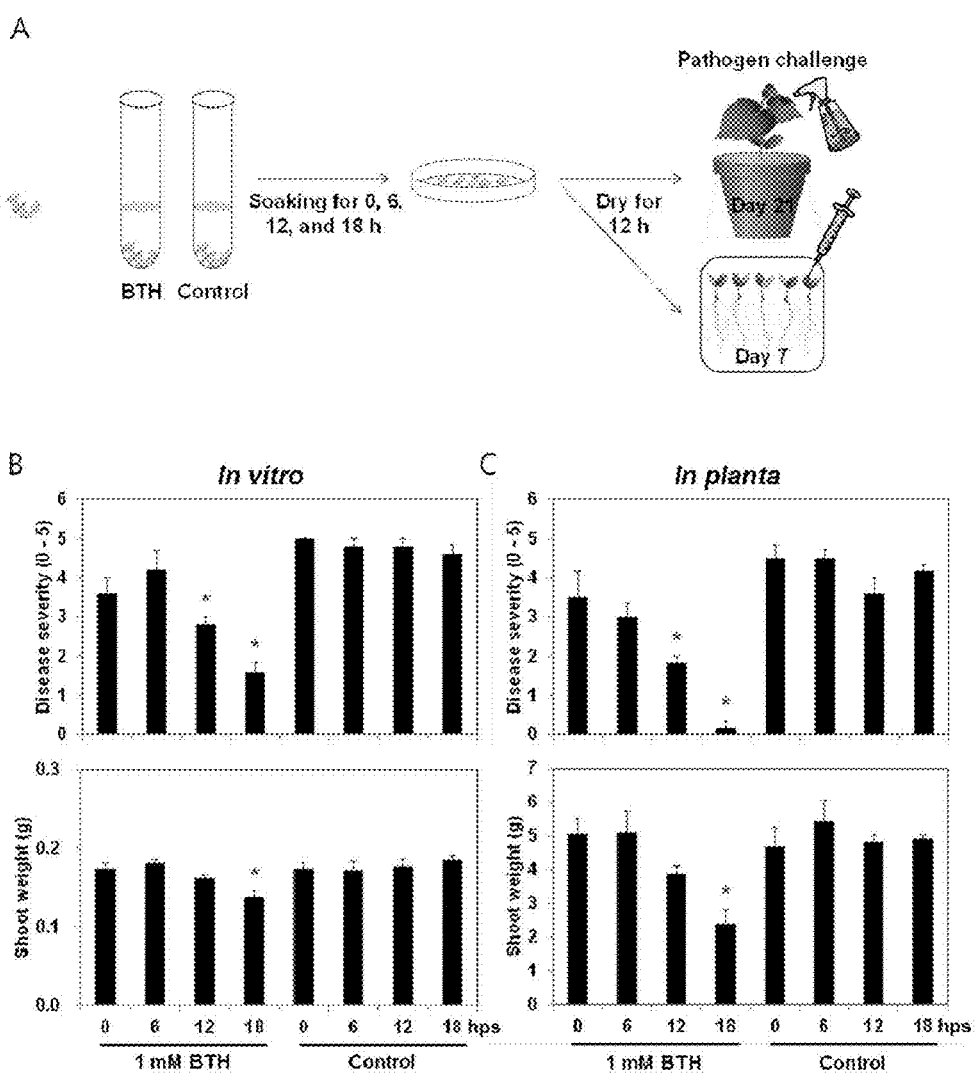
FIG. 1 illustrates a process for optimizing conditions for seed priming by using BTH (benzothiadiazole) to elicit induced systemic resistance against disease without having inhibited growth, and the test results obtained therefrom.

In order to achieve the object of the present invention, the present invention provides *Bacillus* sp. strain PB69 for eliciting induced systemic resistance and promoted growth in a plant. The *Bacillus* sp. strain PB69 has been deposited with Korean Collection for Type Cultures (KCTC) (having the address of 181, Ipsin-gil, Jeongeup-so, Jeollabuk-do, 56212, Republic of Korea) of Korean Research Institute of Bioscience and Biotechnology having the address of 125 Gwahak-ro, Yuseong-gu, Daejeon 305-806, Republic of Korea, under the Access numbers of KCTC 12299BP, on Oct. 30, 2012 (Deposition number: KCTC 12299BP). The deposit has been made and accepted under the terms of the Budapest Treaty and all restrictions imposed by the depositor on the availability to the public of the biological material will be irrevocably removed upon the granting of a patent.

The present invention also provides *Bacillus* sp. strain 1628 for eliciting induced systemic resistance and promoted growth in a plant. The *Bacillus* sp. strain 1628 has been deposited with Korean Collection for Type Cultures (KCTC) (having the address of 181, Ipsin-gil, Jeongeup-so, Jeollabuk-do, 56212, Republic of Korea) of Korean Research Institute of Bioscience and Biotechnology having the address of 125 Gwahak-ro, Yuseong-gu, Daejeon 305-806, Republic of Korea, under the Access numbers of KCTC 12298BP, on Oct. 30, 2012 (Deposition number: KCTC 12298BP). The deposit has been made and accepted under the terms of the Budapest Treaty and all restrictions imposed by the depositor on the availability to the public of the biological material will be irrevocably removed upon the granting of a patent.

The present invention further provides a method of eliciting induced systemic resistance and promoted growth in a plant comprising:

performing high pressure sterilization of culture solution of the *Bacillus* sp. strain PB69 or 1628; and soaking a plant seed in the culture solution of the *Bacillus* sp. strain PB69 or 1628 obtained by high pressure sterilization.

The present invention further provides a method of controlling a plant disease comprising:

performing high pressure sterilization of culture solution of the *Bacillus* sp. strain PB69 or 1628; and soaking a plant seed in the culture solution of the *Bacillus* sp. strain PB69 or 1628 obtained by high pressure sterilization.

According to one embodiment of the present invention, the high pressure sterilization can be performed at 120-130° C. for 15 to 20 minutes, and preferably at 121° C. for 15 minutes, but not limited thereto.

The culture solution according to the present invention is a liquid medium in which *Bacillus* sp. strain PB69 or 1628 of the present invention has been cultured. As for the medium, a medium for culturing microorganisms can be used. Preferably, TSB (Tryptic soy broth) medium can be used, but it is not limited as long as it is a medium containing suitable nutritional components that are required for growth of the *Bacillus* spp. strain. The culture solution may be a culture solution in which *Bacillus* sp. strain PB69 or 1628 has been cultured on a medium for culturing bacteria for 46 to 52 hours at 28 to 32° C. condition, and it is preferably a culture solution in which *Bacillus* sp. strain PB69 or 1628 has been cultured on a TBS medium for 48 hours at 30° C. condition, but not limited thereto. Any method known in the field art can be used as a method for culturing the microbial strains, and it is not particularly limited to any specific method.

According to the present invention, concentration of the *Bacillus* sp. strain PB69 or 1628 in the culture solution can be controlled to $10^7$ to $10^9$ cfu/ml, and preferably $10^8$ to $10^9$ cfu/ml such that the active ingredients are within a biologically effective range, but not limited thereto.

According to the present invention, a seed can be soaked in a culture solution of high pressure-sterilized *Bacillus* sp. strain PB69 or 1628 for 6 to 18 hours, preferably for 10 to 14 hours, and more preferably for 12 hours. However, the soaking time is not limited if it can induce induced systemic resistance and promoted growth or can have an effect of controlling plant diseases.

According to one embodiment of the present invention, a plant disease may develop in a young plant stage, but not limited thereto. The plant diseases can be microbial diseases, preferably pepper bacterial spot or cucumber bacterial spot (cucumber angular leaf spot), and more preferably pepper bacterial spot which is caused by *Xanthomonas axonopodis* pv. *vesicatoria* or cucumber angular leaf spot which is caused by *Psuedomonas syringae* pv. *lachrymans*, but not limited thereto.

The present invention further provides a composition for eliciting induced systemic resistance and promoted growth in a plant or controlling a plant disease containing, as an active ingredient, high pressure-sterilized culture solution of the *Bacillus* sp. strain PB69 or 1628.

The present invention further provides a composition for controlling a plant disease containing, as an active ingredient, high pressure-sterilized culture solution of the *Bacillus* sp. strain PB69 or 1628.

The composition according to one embodiment of the present invention may contain a buffering agent, a carrier, an auxiliary agent, or a diluting agent that are agrochemically allowed, and they are well known in the field. The composition of the present invention may be dried by freeze drying, spray drying, or spray cooling.

The term "buffering agent" is intended to mean an aqueous solution containing a mixture of acid and base which is used for the purpose of stabilizing pH. Examples of the buffering agent which may be used include TRIS, phosphate, carbonate, acetate, citrate, glycolate, lactate, borate, tartarate, cacodylate, ethanolamine, glycine, imidazole, and imidazole lactic acid.

The term "diluent (or carrier)" is intended to mean an aqueous or a non-aqueous solution which is used for the purpose of diluting the high pressure-sterilized culture solution of the *Bacillus* sp. strain PB69 or 1628 described above. The diluent can be at least one of saline, water, polyethylene glycol, propylene glycol, ethanol, or oil (e.g., corn oil, peanut oil, cotton seed oil, or sesame oil).

The term "auxiliary agent" is intended to mean a specific compound added to a formulation for enhancing the biological effect of a composition containing the high pressure-sterilized culture solution of the *Bacillus* sp. strain PB69 or 1628 as an active ingredient.

The diluting agent can be at least one of carbohydrate, polymer, lipid, and inorganic substance. Examples of the carbohydrate include lactose, sucrose, mannitol, and cyclodextrin that are added to a composition for having easy freeze drying.

Examples of the polymer include starch, cellulose ether, cellulose carboxymethyl cellulose, alginate, carrageenan, hyaluronic acid, polyacrylic acid, polysulfonate, polyethylene glycol/polyethylene oxide, polyvinyl alcohol/polyvinyl acetate with different hydrolysis degree, and polyvinylpyrrolidone (including all with different molecular weight).

The composition of the present invention can be prepared in formulation form including an emulsion, an oil emulsion, a wettable powder, a suspension concentrate, a dust, a granule, a tablet, an aerosol, and an ointment, but not limited thereto. If necessary, an emulsifying agent, a suspending agent, a spreader, an infiltrating agent, a wetting agent, a thickening agent, a stabilizing agent, or the like can be blended, and the formulation can be prepared according a production method well known in the field. Preferably, the composition for eliciting induced systemic resistance and promoted growth in a plant or the composition for controlling a plant disease of the present invention can be a formulation in the form of wettable powder or suspension concentrate. More preferably, it can be prepared in liquid form. By adding a bulking agent, it can be used in powder form or it can be formulated to yield a granule. However, it is not particularly limited to those formulations.

The aqueous formulation of the present invention may consist of high pressure-sterilized culture solution of the *Bacillus* sp. strain PB69 or 1628 as an active ingredient, white carbon as a hygroscopic agent, sodium bis[2-ethylhexyl]sulfosuccinate as a wetting agent, sodium lignosulfonate as a dispersing agent, and kaolin as a bulking agent. Preferably, it consists of 10% by weight of the high pressure-sterilized culture solution of the *Bacillus* sp. strain PB69 or 1628, 1% by weight of white carbon, 1% by weight of sodium bis[2-ethylhexyl]sulfosuccinate, 1% by weight of sodium lignosulfonate, and 87% by weight of kaolin, but not limited thereto.

The aqueous liquid formulation of the present invention may consist of high pressure-sterilized culture solution of the *Bacillus* sp. strain PB69 or 1628 as an active ingredient, MBSC (Nonylphenol, ethoxylated, monoether with sulfuric acid, sodium salt, Sodium bis[20 ethylhexyl]sulfosuccinate Polyoxyethylene nonylphenol) as a wetting agent and also as a dispersing agent, isopropanol as a diluting agent, and water as a bulking agent. Preferably, the aqueous liquid formulation may consist of 50% by weight of the high pressure-sterilized culture solution of the *Bacillus* sp. strain PB69 or 1628, 4% by weight of MBSC, 30% by weight of isopropanol, and 16% by weight of water, but not limited thereto.

The term "effective amount" indicates an amount which is sufficient for having a beneficial or desired result, and it can be an amount suitable for eliciting induced systemic resistance and promoted growth in a plant or for controlling *Xanthomonas axonopodis* pv. *vesicatoria* or *Psuedomonas syringae* pv. *lachrymans*. The culture solution may contain *Bacillus* sp. strain PB69 or 1628 at concentration of $10^7$ to $10^9$ cfu/ml such that the active ingredients are within a biologically effective range. Preferably, it may contain *Bacillus* sp. strain PB69 or 1628 at concentration of $10^8$ to $10^9$ cfu/ml or so, but not limited thereto.

The present invention further provides a method for treating a seed to elicit induced systemic resistance and promoted growth in a plant comprising soaking a seed in the aforementioned composition for 6 to 18 hours followed by drying.

The present invention further provides a method for treating a seed to control a plant disease comprising soaking a seed in the aforementioned composition for 6 to 18 hours followed by drying.

According to the present invention, a seed can be soaked in a culture solution which contains, as an active ingredient, high pressure-sterilized *Bacillus* sp. strain PB69 or 1628 for 6 to 18 hours, preferably for 10 to 14 hours, and more preferably for 12 hours. However, the soaking time is not limited if it can induce induced systemic resistance and promoted growth in a plant or can have an effect of controlling plant diseases. Furthermore, a soaked seed of the present invention may be dried at room temperature, but the temperature is not limited as long as germination of a seed is not negatively affected by it. The seed may be dried for 6 to 18 hours, preferably for 10 to 14 hours, and most preferably for 12 hours. However, the time is not limited as long as sufficient drying can be obtained within a range in which germination of a seed is not negatively affected by it The present invention further provides a primed seed produced by the aforementioned method.

According to the "priming" of the present invention, a seed is treated with high pressure-sterilized culture solution of the *Bacillus* sp. strain PB69 or 1628 followed by drying, and thus the effect of eliciting induced systemic resistance and promoted growth and controlling plant diseases can be obtained for the plant grown from the germinated seed. The seed can be preferably a seed of pepper or cucumber, but not limited thereto.

Herein below, the present invention is explained in view of the examples. However, the following examples are given only to illustrate the present invention and by no means the scope of the present invention is limited to them.

EXAMPLES

Materials and Methods

1. Establishment of Conditions for Seed Priming Using BTH

Regarding the priming of a cucumber seed, to establish conditions for seed treatment at which induced systemic resistance against is induced in a plant without inhibiting plant growth, a cucumber seed was treated with BTH (benzothiadiazole), i.e., a potent substance for eliciting resistance, and it was cultivated in a rectangular culture solution dish (125×125 mm) and a pot for determination. The cucumber seed (Bakbong Dadagi, manufactured by Nongwoo Bio, Korea) was subjected to surface sterilization for 5 minutes using 5% NaOCl and, after rinsing 5 times with sterilized water, died on a filter paper. The sterilized seed was soaked for 0, 6, 12, or 18 hours in BTH solution each at 0.1 μM, 10 μM, or 1 mM. 0 Hour means that the seed was dried immediately after soaking. The soaked seed was dried for 12 hours on a culture dish overlaid with a sterilized filter paper. The seed after priming was sown in a pot filled with soil for horticulture (Punong Co., Ltd., Korea) and also in a rectangular culture dish containing distilled water-agar medium (Water agar; WA, plant agar (8 g/L)). Cultivation was continued for 3 weeks for the pot and 1 week for the culture dish in a plant cultivator (12 hour cycle of light and dark, 26° C.), each followed by treatment with pathogens (FIG. 1A). As for the pathogens for cucumber, *Psuedomonas syringae* pv. *lachrymans* was used. The pathogen was cultured for 48 hours at 30° C. on a KB (King's B) solid medium containing 100 μg/ml of Rifampicin. In case of the pot test, the pathogen was sprayed at concentration of $10^{8-9}$ CFU/ml to the leaves. In case of the culture dish test, the pathogen was injected at concentration of $10^{8-9}$ CFU/ml to the leaves, by using a 1 ml syringe (greenject-10). Seven days later, any symptom of disease was determined, and the degree of symptom was measured with scale of from 1 to 5. It is specifically as follows: 0=no symptom, 1=weak whitening symptom, 2=whitening symptom, 3=minor necrosis with whitening symptom, 4=necrosis, and 5=severe necrosis. Stem weight was measured simultaneously with determination of the degree of symptom to see if there is any growth inhibition.

2. Determination of Induced Resistance by Using Culture Solution of Thermally Stable Strains The microbial strain was inoculated to TSB (Tryptic Soy Broth) and cultured for 48 hours in a shaking incubator (200 rpm, 30° C.) (until microbial concentration of $10^8$ to $10^9$ cfu/ml). Then, to use only thermally stable substances, it was subjected to a high pressure sterilization at 121° C. for 15 minutes. After soaking the seed for 12 hours in culture solution of 553 high pressure-sterilized strains, it was dried for 12 hours and the induced resistance and degree of inhibited growth in a plant which has been germinated on the rectangular culture solution dish were determined (FIG. 2A). By using *Psuedomonas syringae* pv. *lachrymans* transformed with a green fluorescent protein (GFP) gene as a pathogen, GFP expression was quantitatively determined based on an image analysis.

3. Measurement of Expression Amount of Plant Disease Resistance-Related Gene

In order to measure an expression amount of a plant disease resistance-related gene, pathogen was inoculated to a cucumber, and sampling was made 0, 3 or 24 hours later. Total RNA was isolated from the sampled cucumber leaf by using RNeasy Plus Mini Kit (50). cDNA was synthesized from 2 μg of the RNA by using an oligo-dT primer and MMLV-RT (Moloney murine leukemia virus reverse transcriptase, Enzynomics, KOREA). cDNA was then used for qRT-PCR (quantitative Reverse Transcriptase Polymerase Chain Reaction) based on Chromo4 Real Time PCR system (BIO-RAD) by using each primer for the genes of LOX, PR2 and ETR that are known to be related to resistance to diseases. LOX primer is as follows; forward direction: 5'-AAGGTTTGCCTGTCCCAAGA-3' (SEQ ID NO: 1) and reverse direction: 5'-TGAGTACTGGATTAACTCCAGC-CAA-3' (SEQ ID NO: 2), PR2 primer is as follows; forward direction: 5'-TCAATTATCAAAACTTGTTCGATGC-3' (SEQ ID NO: 3) and reverse direction: 5'-AACCG-GTCTCGGATACAACAAC-3' (SEQ ID NO: 4), and ETR primer is as follows; forward direction: 5'-GCCATTGTTG-CAAAAGCAGA-3' (SEQ ID NO: 5) and reverse direction: 5'-GCCAAAGACCACTGCCACA-3' (SEQ ID NO: 6).

4. Determination of Selected Strains by Pot Test

The microbial strains selected according to confirmation of degree of induced resistance and inhibited growth in the plant, which has been obtained by soaking a seed in a heat-treated microbial culture solution followed by germination, were determined again by a method of determining disease resistance of a plant grown in the pot. Specifically, the pathogen was sprayed onto the 3-week old pot plant, and sampling was made on Day 0, Day 3, or Day 7. After spreading on KB medium added with Rifampicin, number of the pathogen was counted. Furthermore, on Day 7 after treatment with pathogen, stem weight was measured. For each sample obtained 0 or 6 hours after the inoculation of pathogen, qRT-PCR was performed in the same manner as above to confirm the expression of LOX and PR2 genes.

5. Large Scale Field Determination Using Cucumber

By using the high pressure-sterilized culture solution of selected strains, BTH as a positive control, and TSB and water as a negative control, a large scale determination of a cucumber plant was performed. Seed primed with each treatment group was cultivated in a 32-hole tray and transplanted in an outdoor field. Then, stem length was measured on the transplantation day (day after transplant, DAT), and the measurement was continuously made at an interval of 10 days. On 30 DAT, the cultured pathogen was sprayed at concentration of $10^{8-9}$ CFU/ml in the same manner as above to the plant leaf, and any symptom of diseases was confirmed 7 days after the inoculation of the pathogen. On 35 DAT, the harvest amount was measured. On 50 DAT, weight of the whole stem was measured.

6. Large Scale Field Determination Using Pepper

In order to see if there is the same effect shown for other crops, a large scale determination was performed by using pepper. The pepper seed (Pukang pepper, Hungnong, Korea) was soaked for 48 hours, and then the following procedures were performed in the same manner as the cucumber seed priming to see the induced resistance and growing state. The pepper seed which has been primed with each treatment group (i.e., high pressure-sterilized culture solution of selected strains, BTH as a positive control, and TSB and water as a negative control) was cultivated for a month in a 32-hole tray, and then transplanted in a field in which peppers were grown for several years. From day 20 to day 70 after the transplantation, length of the plant stem was measured at an interval of 10 days, and peppers were harvested twice on 80 DAT and 100 DAT. For determination of resistance to disease, *Xanthomonas axonopodis* pv. *vesicatoria* was used as pepper pathogen, and a method of infiltrating $10^6$ cfu/ml suspension into a back side of leaf by using a syringe was used. Any symptom of disease was determined generally 7 days after the inoculation of the pathogen. Degree of symptom was determined as level of from 0 to 5, similar to the cucumber. On 20 DAT, 30 DAT, and 40 DAT, a treatment with pathogen was performed with the same method to determine resistance to disease.

Example 1

Establishment of Conditions for Seed Priming Using BTH

To establish conditions for seed priming at which induced systemic resistance against disease is induced in a plant without inhibiting plant growth, a test was performed by using BTH, a potent substance for inducing resistance. The cucumber seed treatment for eliciting induced systemic resistance both in vitro and in planta was found to be most effective when soaking in 1 mM BTH is performed for 12 hours and 18 hours for each case. To confirm the inhibited growth which occurs at the time of having induced systemic resistance, stem weight was measured. As a result, it was found that, compared to a control group in which sterilized water is used, the growth inhibition is shown with a statistic significance when the seed was treated with 1 mM BTH for 18 hours (FIG. 1). Thus, soaking in 1 mM BTH for 12 hours at which no growth inhibition is shown while having induced systemic resistance was selected as an optimum condition for seed priming.

Example 2

Selection of Microbial Strains for Eliciting Induced Systemic Resistance

Figure 2:
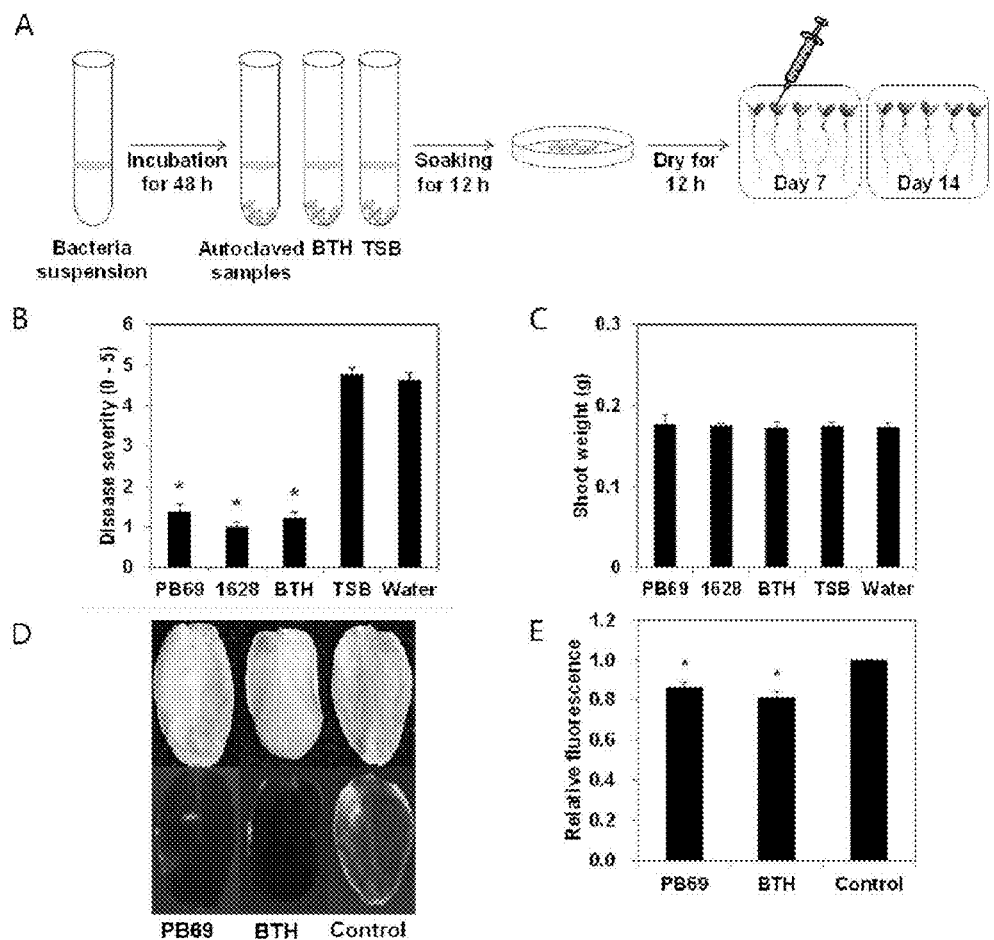
FIG. 2 illustrates a result obtained from strain selection which is made in view of the resistance to disease and growth level of a seed which has been soaked for 12 hours in any one of high pressure-sterilized culture solution of 553 strains, BTH as a positive control, or TBS medium as a negative control. Specifically, *Psuedomonas syringae* pv. *lachrymans* containing with GFP gene was inoculated to a primed plant, and the pathogen growth was determined based on the level of GFP expression.

With the selected optimum priming conditions, a seed was soaked in each high pressure-sterilized culture solution of 553 microbial strains followed by drying. Then, induced systemic resistance and growth level were measured for the germinated plants. As a result, the high pressure-sterilized culture solution of PB69 or 1628 strain exhibited the effect of eliciting induced systemic resistance at almost the same level as that obtained from the priming treatment using BTH. To confirm growth inhibition which is exhibited during induction of induced systemic resistance, stem weight was measured. As a result, it was found that there is no growth inhibition in the treatment group compared to a control. Furthermore, to confirm the effect of controlling pathogens by the high pressure-sterilized culture solution of the aforementioned strains, a cucumber plant was inoculated with *Psuedomonas syringae* pv. *lachrymans* added with GFP and a fluorescent image was taken for each treatment group. As a result, it was visually confirmed that GFP expression is lower in the PB69 treatment group compared to a control. According to quantitative GFP analysis, GFP expression was also found to be low in PB69 treatment group (FIG. 2).

Example 3

Measurement of Expression Amount of Plant Disease Resistance-Related Gene

Figure 3:
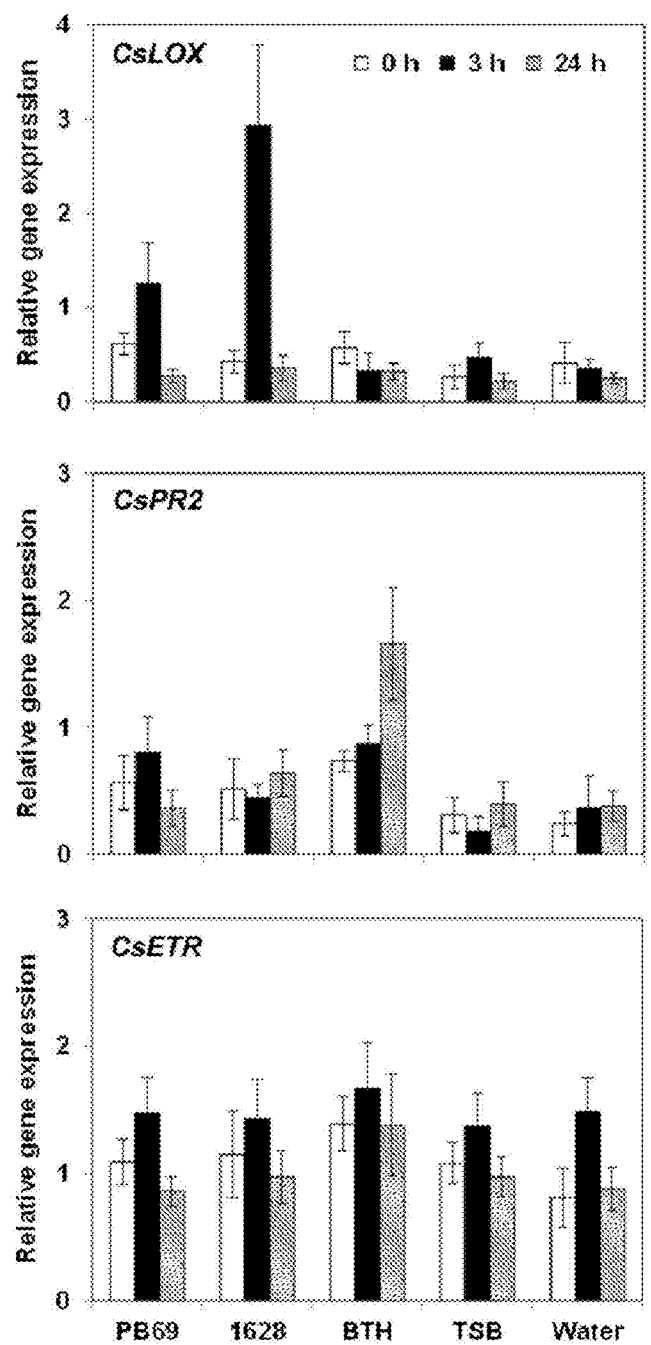
FIG. 3 illustrates a result of determining expression of LOX, PR2, and ETR, which are the genes relating to resistance against plant disease, by qRT-PCR.

In order to measure an expression amount of a plant disease resistance-related gene, qRT-PCR was performed by using primers for LOX, PR2 and ETR that are known to be related to resistance to plant diseases. Level of expression of each gene was determined 0, 3, or 24 hours after the inoculation of the pathogen (*Psuedomonas syringae* pv. *lachrymans*) to a cucumber plant (FIG. 3). Expression level of LOX gene was found to be 1.3 and 2.9 for PB69 and 1628 treatment group, respectively, three hours after the inoculation of the pathogen. It is higher by 2.6 times or 5.8 times than the expression level of TSB treatment group (0.5), which is a negative control. In the BTH treatment group, expression level of LOX gene was close to that of a negative control, similar to previous experiments. In case of PR2, the expression level was found to be 1.7 in the BTH treatment group after 24 hours, and thus it is higher by 4.3 times than water (0.4), which is a negative control. Both in PB69 and 1628 treatment groups, there was a slight increase compared to a negative control. Meanwhile, there was no difference in expression of ETR gene among different treatment groups.

Example 4

Determination of Selected Microbial Strains Based on Pot Test

Figure 4:
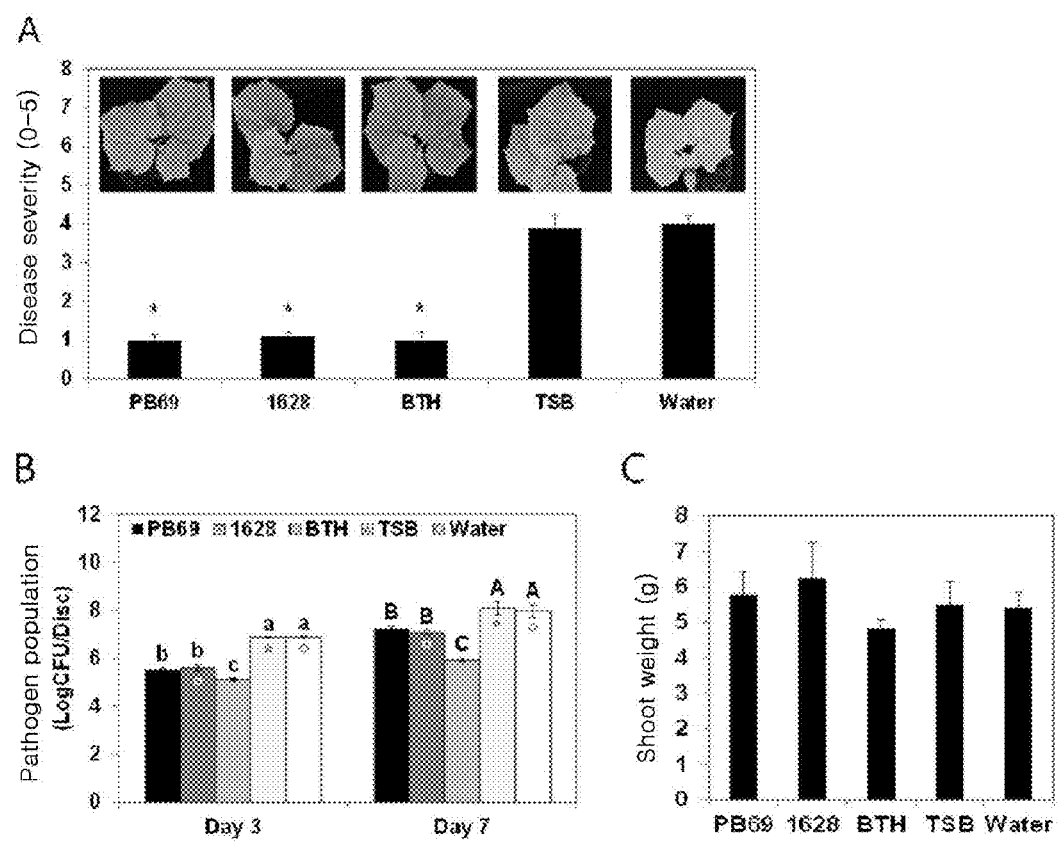
FIG. 4 illustrates a result of determining induced resistance of a cucumber plant of which seeds have been primed with a high pressure-sterilized culture solution of strain PB69 or 1628.

By using high pressure-sterilized culture solution of the selected microbial strain PB69 or 1628, a test was carried out to see if it can induce induced systemic resistance in a plant grown in a pot, before performing a large scale determination. As a result, it was found that the cucumber seed which has been primed with each of high pressure-sterilized culture solution of the strains PB69 and 1628 exhibited resistance to a disease, similar to the in vitro case. When the cucumber grown in a pot after the seed priming was treated with pathogens (*Psuedomonas syringae* pv. *lachrymans*) and number of the pathogen was counted day 3 and day 7, it was found that the number of the pathogen was reduced in the PB69 or 1628 compared to a control. Even though there was no significant difference in stem weight, it was higher in the PB69 or 1628 treatment group compared to the BTH treatment group (FIG. 4).

Example 5

Large Scale Determination Using Cucumber

Figure 5:
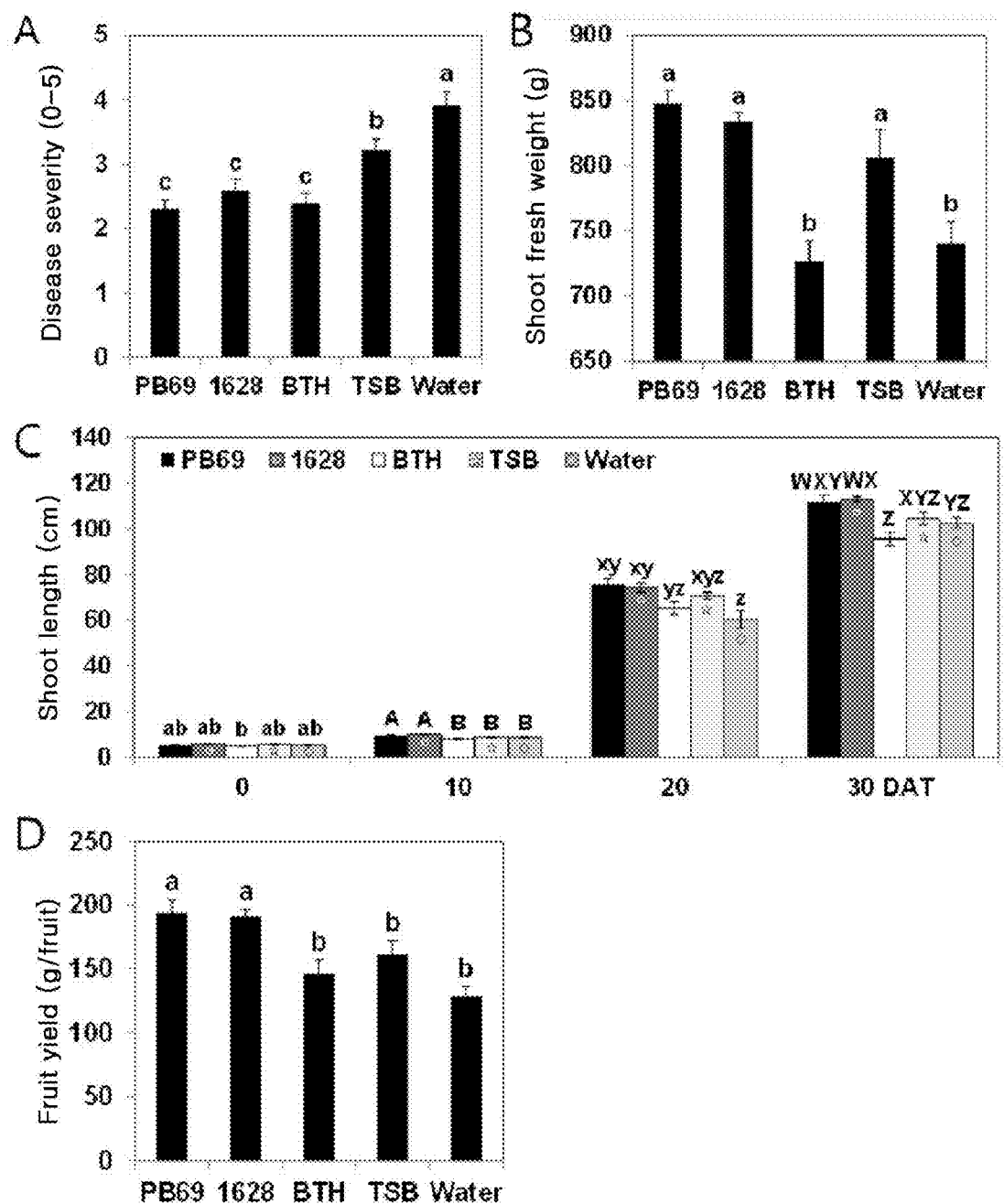
FIG. 5 illustrates a result of a large-scale field test on the induced resistance to disease and promoted growth of a cucumber plant of which seeds have been primed with a high pressure-sterilized culture solution of strain PB69 or1628.

By using the high pressure-sterilized culture solution of selected strain PB69 or 1628, BTH as a positive control, and TSB and water as a negative control, a large scale determination of a cucumber plant was performed. As a result, it was found that on 30 DAT, resistance to disease is induced in the group which has been treated with high pressure-sterilized culture solution of PB69 or 1628 strain. The stem length was measured at an interval of 10 days from 0 DAT to 30 DAT. As a result, on 0 DAT, there was no difference in growth between the group treated with the high pressure-sterilized culture solution of selected strain PB69 or 1628 and a control. However, on 10 DAT, it was confirmed that the length of the treatment group has grown with a statistic significance compared to a control. Furthermore, on 20 DAT, it was confirmed that the plant growth is promoted in the group treated with high pressure-sterilized culture solution of the strain PB69 or 1628 compared to the water treatment group, but it was not much different compared to the BTH and TSB treatment groups. On 30 DAT, it was confirmed that, with a statistic significance, the plant growth is promoted in the group treated with high pressure-sterilized culture solution of the strain PB69 or 1628 compared to the group treated with BTH, a potent substance for inducing resistance. It was also confirmed that, with a statistic significance, the cucumber harvest amount is higher in the group treated with high pressure-sterilized culture solution of the strain PB69 or 1628 compared to a control (FIG. 5).

Example 6

Large Scale Determination Using Pepper

Figure 6:
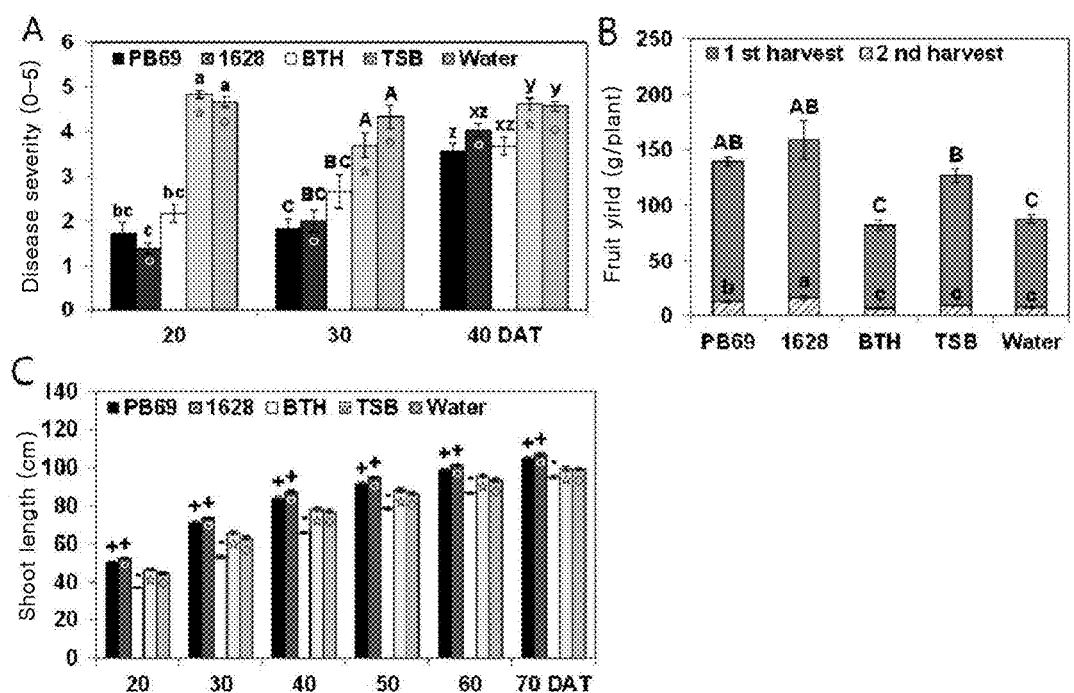
FIG. 6 illustrates a result of a large scale test on the induced resistance to disease and promoted growth of a pepper plant of which seeds have been primed with a high pressure-sterilized culture solution of strains PB69 and 1628.

In order to see whether or not the high pressure-sterilized culture solution of the strain PB69 or 1628 exhibits the same effect as above in other crops, a large scale test was performed by using pepper. As a result, it was able to confirm that disease resistance is induced on 20 DAT, 30 DAT, and 40 DAT in a plant of which seed has been primed with high pressure-sterilized culture solution of the strain PB69 or 1628. In terms of the first harvest (80 DAT), there was no significant difference in harvest amount between the group treated with high pressure-sterilized culture solution of the strain PB69 or 1628 and the TBS treatment group. However, the harvest amount was significantly increased compared to the BTH and water treatment groups. According to the second harvest (100 DAT), it was able to confirm that the harvest amount is increased in the group treated with high pressure-sterilized culture solution of the strain PB69 or 1628 compared to a control. As a result of measuring the length of pepper plant from 20 DAT to 70 DAT at an interval of 10 days, it was confirmed that from the transplantation day to 70 DAT, the group treated with high pressure-sterilized culture solution of the strain PB69 or 1628 exhibits promoted growth compared to a control group (FIG. 6).

The invention claimed is:

1. A method of inducing systemic resistance and promoting growth in a plant, the method comprising:
   performing high pressure sterilization of a culture solution of the *Bacillus* sp. strain PB69 (KCTC 12299BP); and
   soaking a plant seed in the culture solution of the *Bacillus* sp. strain PB69 (KCTC 12299BP) obtained by the high pressure sterilization.

2. The method of of claim 1, wherein the high pressure sterilization is performed at 120 to 130° C. for 15 to 20 minutes.

3. A method of controlling a plant disease, the method comprising:
   performing high pressure sterilization of a culture solution of the *Bacillus* sp. strain PB69 (KCTC 12299BP); and
   soaking a plant seed in the culture solution of the *Bacillus* sp. strain PB69 (KCTC 12299BP) obtained by the high pressure sterilization.

4. The method of claim 3, wherein the plant disease is pepper bacterial spot or cucumber angular leaf spot.

5. A composition comprising a high pressure-sterilized culture solution of the *Bacillus* sp. strain PB69 (KCTC 12299BP) as an active ingredient.

6. A method for treating a seed to induce systemic resistance and promote growth in a plant comprising soaking the seed in the composition of claim 5 for 6 to 18 hours followed by drying.

7. A primed seed produced by the method of claim 6.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
aaggtttgcc tgtcccaaga                                              20

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
tgagtactgg attaactcca gccaa                                        25

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tcaattatca aaacttgttc gatgc                                        25

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
aaccggtctc ggatacaaca ac                                           22

<210> SEQ ID NO 5
<211> LENGTH: 20
```

```
<212> TYPE: DNA
<213> ORGANISM: Artificial Sequence
<220> FEATURE:
<223> OTHER INFORMATION: Primer

<400> SEQUENCE: 5
gccattgttg caaaagcaga                                                    20

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
gccaaagacc actgccaca                                                     19
```